(12) United States Patent
Ketola et al.

(10) Patent No.: US 9,090,862 B2
(45) Date of Patent: Jul. 28, 2015

(54) SYSTEM AND METHOD FOR PROCESSING BIOLOGICAL MATERIAL

(71) Applicant: Ductor Oy, Helsinki (FI)

(72) Inventors: Ari Ketola, Espoo (FI); Veikko Latvala, Vahto (FI)

(73) Assignee: Ductor Oy, Helsinki (FI)

( * ) Notice: Subject to any disclaimer, the term of this patent is extended or adjusted under 35 U.S.C. 154(b) by 17 days.

(21) Appl. No.: 13/937,888

(22) Filed: Jul. 9, 2013

(65) Prior Publication Data

US 2014/0178972 A1    Jun. 26, 2014

Related U.S. Application Data

(60) Provisional application No. 61/740,833, filed on Dec. 21, 2012.

(51) Int. Cl.
*C12N 1/12* (2006.01)
*C12M 1/00* (2006.01)
(Continued)

(52) U.S. Cl.
CPC ............ *C12M 21/02* (2013.01); *C12M 23/18* (2013.01); *C12M 23/22* (2013.01); *C12M 23/36* (2013.01);
(Continued)

(58) Field of Classification Search
CPC ...... C12M 21/02; C12M 21/12; C12M 23/06; C12M 23/18; C12M 23/22; C12M 23/26; C12M 23/36; C12M 23/58; C12M 41/24; C12M 41/34; C12M 41/40; C12M 47/06; C12N 1/12
See application file for complete search history.

(56) References Cited

U.S. PATENT DOCUMENTS 2,732,663 A * 1/1956 Dewey, II .................. 47/1.4
4,868,123 A * 9/1989 Berson et al. ........... 435/286.6
(Continued)

FOREIGN PATENT DOCUMENTS

CN    201224730 Y    4/2009
CN    102286362 A    12/2011
(Continued)

OTHER PUBLICATIONS

Veikko Latvala et al., the Specification, Claims, and Drawings of unpublished U.S. Appl. No. 13/722,228, filed Dec. 20, 2012, which is considered to be a related application to the subject application.
(Continued)

*Primary Examiner* — William H Beisner
(74) *Attorney, Agent, or Firm* — Lucas & Mercanti LLP; Robert P. Michal (57) ABSTRACT

The invention provides an algae cultivation system and a process for cultivating algae. The algae cultivation system includes a conduit system having a first portion exposed to illumination and a second portion occluded from illumination that is capable of containing and moving a first type of algae, and a heat exchanger in thermal contact with the second portion of the conduit system. The algae cultivation system also includes a vertical conduit connected to the first portion of the conduit system and extending vertically upward from the first portion of the conduit system, a gas collection chamber communicating with an upper end region of the vertical conduit, and an algae processing unit that is capable of processing algae from the first portion of the conduit system, and that directs the extracted sugar, water and nutrients into the second portion of the conduit system to interact with the second type of algae therein.

20 Claims, 7 Drawing Sheets

(51) Int. Cl.
*C12M 1/02* (2006.01)
*C12M 1/34* (2006.01)
*C12M 1/107* (2006.01)

(52) U.S. Cl.
CPC .............. *C12M 23/58* (2013.01); *C12M 41/24* (2013.01); *C12M 41/34* (2013.01); *C12M 41/40* (2013.01); *C12M 47/06* (2013.01); *C12N 1/12* (2013.01)

(56) References Cited

U.S. PATENT DOCUMENTS

| 5,354,878 | A | 10/1994 | Connemann et al. | |
| 6,492,149 | B1* | 12/2002 | Muller-Feuga | 435/173.8 |
| 7,777,085 | B2 | 8/2010 | Berry et al. | |
| 7,977,076 | B2 | 7/2011 | Oyler | |
| 8,287,732 | B2 | 10/2012 | Chen et al. | |
| 2011/0223644 | A1 | 9/2011 | Kodukula et al. | |
| 2013/0177966 | A1* | 7/2013 | De Poli | 435/252.1 |

FOREIGN PATENT DOCUMENTS

| ES | 2150389 A1 | 11/2000 |
| WO | WO 2010/014797 A2 | 2/2010 |

OTHER PUBLICATIONS

PCT International Search Report mailed Apr. 28, 2014 which is issued in a related PCT International Patent Application No. PCT/IB2013/061233, filed Dec. 20, 2013 (10 pages).

* cited by examiner

SYSTEM AND METHOD FOR PROCESSING BIOLOGICAL MATERIAL

The present application claims the benefit of U.S. provisional patent application Ser. No. 61/740,833, filed on Dec. 21, 2012, the contents of which are incorporated by reference herein in its entirety.

TECHNICAL FIELD

The present invention relates generally to systems and processes for cultivating biological material and more specifically to systems and processes for cultivating algae.

BACKGROUND OF THE INVENTION

It has been proposed to cultivate biological material such as algae on a large scale to provide an efficient and sustainable source of nutrients, chemical feedstocks and/or fuel, e.g., biogas, biocrude or biodiesel. The advantages of algae are that it can be cultivated in salt water, brackish water or fresh water and represents a source of biomass and oils that is potentially carbon neutral, that takes up little or no arable land, and will not displace conventional food crops from the marketplace. Despite many previous attempts, unfortunately, it has proved difficult to cultivate algae in an economical and cost effective manner.

One previous approach has been to try to harvest both biomass and oils from an algae crop. For example, U.S. Pat. No. 8,287,732 discloses a method where algae is cultivated, oils extracted for conversion to biofuel, and then the residual biomass hydrolyzed and anaerobically digested to extract nutrients such as carbon dioxide and compounds containing nitrogen and phosphorous to be recycled back into the algae cultivation process. Recovery and reuse of nutrients from biomass remaining after lipid extraction by hydrolysis or anaerobic digestion is also described by this patent.

U.S. Pat. No. 7,977,076 describes a multi-stage algae cultivation process for producing biodiesel and/or bioethanol. In this cultivation process, a first type of algae was cultivated autotrophically (under light) and then converted into feed for a second type of algae that produces oil, wherein the oil is extracted and converted to biodiesel. Both the '732 patent and the '076 patent are incorporated by reference herein.

Nevertheless, obstacles remain to achieving cost-effective integrated algae cultivation to produce biothels and the like. In particular, the control of temperature, carbon dioxide ($CO_2$) and oxygen ($O_2$) levels during cultivation remains a challenge. Algae requires relatively stable temperatures and gas levels to maintain optimal growth conditions. While $CO_2$ is a desirable nutrient to support photosynthetic growth, $CO_2$ must be held within an optimal percentage of the circulating gas mixture, e.g., from about 10-13 (vol %) have found to be convenient for *Chlorella* sp. growth (Hulatt, C. J., et al., 2012. *Bioenergt Resources* 5: 669-684; Douskova, I., et al., 2008 "Microalgae as a means for converting flue gas CO2 into biomass with a high content of starch." *Bioenergy: Challenges and Opportunities International Conference and Exhibition on Bioenergy.* Apr. 6-9, 2008. Universidade do Minho, Guimarães, Portugal). In addition, $O_2$ is a byproduct of photosynthesis, but $O_2$ levels in the aqueous medium an the algae cultivation system should be kept below about 400% of the air saturation value (Chisti, Y. 2007 *Biotechnology Advances* 25: 294-306.) in order to avoid deleterious effects for algae cultivation in a closed system.

Thus, there remains a longstanding need in the art for solutions that provide for the economically efficient cultivation of algae, while addressing these previous shortcomings.

SUMMARY OF THE INVENTION

Accordingly, in a first embodiment, the invention provides for an algae cultivation system, comprising:

a conduit system having a first portion exposed to illumination and a second portion occluded from illumination;

a flow mechanism capable of causing movement of a first type of algae, in an aqueous medium, through said first portion of said conduit system;

a heat exchanger in thermal contact with said second portion and capable of passing the first type of algae, in an aqueous medium, to thereby enable heat transfer between the first portion and the second portion of the conduit system;

a source of algae nutrients;

a first flow regulating system that is capable of regulating flow of algae nutrients from said source of algae nutrients into said first portion of said conduit system;

a source of carbon dioxide;

a second flow regulating system that is capable of regulating flow of carbon dioxide from said source of carbon dioxide into said first portion of said conduit system;

a vertical conduit connected to said first portion of said conduit system and extending vertically upward from said first portion of said conduit system to introduce hydrostatic pressure to the first portion of said conduit system;

a gas collection chamber communicating with an upper end region of said vertical conduit, said second flow regulating system being controlled based on characteristics of gas in said gas collection chamber; and an algae processing mechanism that is capable of processing algae from said first portion of said conduit system to extract sugar, water and nutrients and directing the extracted sugar, water and nutrients into said second portion of the conduit system to interact with the second type of algae therein;

wherein the first portion is partially or entirely transparent to the illumination.

optionally, a third flow regulating mechanism is provided, that is capable of regulating flow of oxygen from the gas collection chamber into the interior of the heat exchanger to interact with the second type of algae therein;

wherein the first portion is partially or entirely transparent to the illumination.

In a further embodiment, the second portion of the conduit system of the algae cultivation system is optionally situated underground. In an underground location, the second portion is occluded from light, and in certain embodiments, the underground location provides the added benefit of thermal stability provided by the surrounding earth. Optionally, the same thermal stability is obtained by locating the second portion in other locations surrounded by sufficient mass for thermal regulation, e.g., tanks of water, body of water (ocean, lake, river) concrete blocks, packed gravel, and the like.

In one embodiment, the first portion optionally includes a plurality of elongate conduits substantially parallel to one another and connected at adjacent ends to form a serpentine travel path for the flow of aqueous medium comprising the first type of algae.

In another embodiment, the flow regulating mechanism includes a pump associated with the first portion of the conduit system and that enables a variable speed of algae flow through the first portion of the conduit system.

In another embodiment, the second flow regulating system includes a motor and a compressor/valve controlled by the motor, the motor being controlled by command signals generated based on the characteristics of the gas in the gas collection chamber.

In another embodiment, the algae cultivation system includes a measurement sensor associated with the gas collection chamber for measuring carbon dioxide in the gas collection chamber and generating the command signals for the motor based thereon.

In another embodiment, the vertical conduit of the algae cultivation system is from about 10 meters to about 30 meters in height extending upward from the conduit system.

In another embodiment, the algae cultivation system, further includes a first type of algae in the first portion, and a second type of algae in the second portion, wherein the first and the second type of algae, respectively, are suspended in a suitable aqueous medium.

The invention further includes processes for the cultivation of algae with the inventive apparatus of claim 1, including the steps of:
(a) growing type 1 algae in an aqueous medium in the first portion,
  (i) harvesting the type 1 algae from the aqueous medium, and
  (ii) recovering carbohydrates from cells of the harvested type 1 algae;
(b) growing type 2 algae in an aqueous medium in the presence of sufficient nutrients to promote heterotrophic growth, in the portion, wherein the nutrients comprise carbohydrates extracted from the type 1 algae, and/or oxygen collected from the gas collection chamber,
  (i) harvesting type 2 algae from the aqueous medium of the second reservoir, and
  (ii) recovering lipids, proteins, and/or carbohydrates from cells of the harvested type 2 algae.

In a preferred embodiment, the illumination of the first portion is from sunlight. In this embodiment, sunlight imparts thermal energy to the first portion and the thermal energy is distributed to the second portion to maintain temperatures in a range of from about 20° C. to about 45° C.

DETAILED DESCRIPTION OF THE INVENTION

The present invention provides apparatus and integrated processes for cultivating algae. In order to more clearly appreciate the invention, the following terms are defined. The terms listed below, unless otherwise indicated, will be used and are intended to be defined as indicated. Definitions for other terms can occur throughout the specification.

As used herein, it is intended that all singular terms also encompass the plural, active tense and past tense forms of a term, unless otherwise indicated.

As used herein the term "algae" refers to a large and diverse group of typically heterotrophic, eukaryotic organisms that can be found growing in fresh, salt or brackish water. While the group encompasses multicellular seaweeds, the algae referred to herein are preferred to belong to the unicellular variety, i.e., microalgae. Generally, the term "algae" as employed herein references microalgae, unless otherwise indicated. Algae are promising bioenergy feedstock alternative to terrestrial crops, as microalgae have high photosynthetic efficiency, high growth rate, low requirement for cultivation area, low water demand. Moreover, some algae are able to grow heterotrophically without light, and use carbohydrates such as glucose as a food source. Furthermore, in heterotrophic culture the lipid content of the produced is usually higher than in autotrophic culture.

In addition, algae is considered an example of biological material that may be cultivated in accordance with the invention, but the invention covers other biological materials.

A "type 1 algae" according to the invention is an algae that preferably produces carbohydrates in autotrophic growth, that can be extracted and fed to a "type 2 algae". Preferred type 1 algae that are high sugar producers when grown autotrophically include, for example, *Scenedesmus dimorphus, Porphyridium cruentum* and *Chlorella protothecoide.*

A type 2 algae (heterotrophic) is selected to be capable of growth in the absence of sufficient light to support photosynthesis, and to produce lipids, i.e., oils that can be harvested and processed into biofuels, e.g., biodiesel or biocrude. Preferred type 2 algae that are high oil producers include, for example, *Chlorella, Spirulina, Chlamydomonas* and *Scenedesmus,* among others.

Lipid or oil-producing algae can include a wide variety of algae, although not all algae produce sufficient oil. The most common oil-producing algae can generally include, or consist essentially of, the diatoms (bacillariophytes), green algae (chlorophytes), blue-green algae (cyanophytes), and golden-brown algae (chrysophytes). In addition a fifth group known as haptophytes may be used. Specific non-limiting examples of bacillariophytes capable of oil production include the genera *Amphipleura, Amphora, Chaetoceros, Cyclotella, Cymbella, Fragilaria, Hantzschia, Navicula, Nitzschia, Phaeodactylum,* and *Thalassiosira.* Specific non-limiting examples of chlorophytes capable of oil production include *Ankisirodesmus, Botryococcus, Chlorella, Chlorococcum, Dunaliella, Monoraphidium, Oocystis, Scenedesmus,* and *Tetraseimis.* In one aspect, the chlorophytes can be *Chlorella* or *Dunaliella.* Specific non-limiting examples of cyanophytes capable of oil production include *Oscillaioria* and *Synechococcus.* A specific example of chrysophytes capable of oil production includes *Boekelovia.* Specific non-limiting examples of haptophytes include *Isochrysis* and *Pleurochysis.*

Preferred type 2 algae that are high oil producers include, for example. *Chlorella, Spirulina, Chlamydomonas* and *Scenedesmus,* among others. Algae suitable for biodiesel production include, e.g., *Chlorella (C. vulgaris, C. protothecoides), Botrycoccus, Scenedesmus, Ankistrodesmus, Dunaliella, Galdieria, Spirulina, Crypthecodinium.*

A number of algae, including those listed supra, can serve as either type 1 or type 2 algae, depending on the growth conditions. For example, it is known that, the lipid content of Chlorella algae can be increased by exposing the algae to stress conditions such as darkness or nutrient depletion. In autotrophic culture the lipid content of Chlorella is usually lower than the carbohydrate content. Additional algae useful according to the invention include, those listed by Table 1.

TABLE 1

| | Lipids (%) | Carbohydrates (%) | Properties |
|---|---|---|---|
| Botryococcus braunii | 29-75 | | autotrophic and heterotrophic |
| Chlorella vulgaris | 14-22 in some cases 70% (N starvation) | 12-17 | autotrophic and heterotrophic |
| Chlorella protothecoides | 15-55 | | autotrophic and heterotrophic |
| Scenedesmus dimorphus | 16-40 | 21-52 | autotrophic |
| Chlamydomonas reinhardtii | 21 | 17 | |
| Porphyridium cruentum | 9-14 | 40-57 | salt option for sugar production |
| N-fixing cyanobacteria | | | |
| Spirulina maxima | 5-6 | 13-16 | can use ammonia as a nitrogen source |
| Spirulina platensis | 5-6 | 8-14 | |

As used herein, the term "reaction" is intended to cover single step and multi-step reactions which can be direct reactions of reactants to products or may include one or more intermediate species which can be either stable or transient.

As used herein, the term "biofuel" refers to any fuel, fuel additive, aromatic, and/or aliphatic compound derived from a biomass starting material such as algae, corn, switchgrass, or the like.

As used herein, the term "biocrude" refers to the oils or fats extracted from plant or animal material, such as algae.

As used herein, the term "biodiesel" refers to a fuel intended to be a replacement for conventional diesel fuel, that is prepared from plant or animal oils or fats. Biodiesel most commonly consists of long-chain esters, i.e., fatty acid esters. These are most commonly prepared by transesterification.

As used herein, the term "transesterify," "transesterifying," and "transesterification" refer to a process of exchanging an alkoxy group of an ester by another alcohol and more specifically, of converting algal oil, e.g. triglycerides, to biodiesel, e.g. fatty acid alkyl esters, and glycerol. Transesterification can be accomplished by using traditional chemical processes such as acid or base catalyzed reactions, or h using enzyme-catalyzed reactions and is contemplated as one of several art-known methods of converting algal oils to useful biofuels. See, simply by way of example, U.S. Pat. Nos. 5,354,878 and 7,777,085, incorporated by reference herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight range of about 1% to about 20% should be interpreted to include not only the explicitly recited concentration limits of 1% to about 20%, but also to include individual concentrations such as 2%, 3%, 4%, and sub-ranges such as 5% to 15%, 10% to 20%, etc.

As used herein, the term "conduit" or any variation thereof, includes any structure through which a fluid may be conveyed. Non-limiting examples of conduit include pipes, tubing, channels, or other enclosed structures, that may exhibit a circular or non-circular cross section. For the cultivation of algae under autotrophic conditions, the conduit requires an aspect that will allow light to illuminate algae present in the conduit, e.g., in an aqueous medium, e.g., the conduit is made of a transparent glass or polymer, in part or in whole.

As used herein, the term "fluid" encompasses a liquid or gas.

As used herein, the term, "aqueous medium" encompasses fresh water, brackish water and/or salt or ocean water that is suitable for growth of algae according to the invention. The aqueous medium may also include appropriate art-known fertilizer for promoting the growth of algae, e.g., nitrates or ammonia or ammonium, phosphorous fertilizers and/or potassium, and the like, in concentrations suitable for promoting the growth of algae. The aqueous medium may also include appropriate nutrients such as sugars, in amounts effective for feeding the algae, and particularly for feeding the type 2 algae.

As used herein, the term "reservoir" or any variation thereof includes any body structure capable of retaining fluid. Non-limiting examples of reservoirs include ponds, tanks, lakes, tubs, or other similar structures. For the cultivation of algae under autotrophic conditions, the reservoir requires an aspect (e.g., in whole or in part) that will allow light to illuminate the algae in an aqueous medium, e.g., an open top, a transparent glass or polymer top, side or bottom.

Accordingly, in one embodiment, the invention provides for a process for growing algae by separately cultivating two or more volumes of algae under conditions, and with an algae growth apparatus designed to integrate the temperature control, $CO_2$ and $O_2$ levels and nutrient flows among the two or more separately cultivated volumes. In this embodiment, the process broadly includes:

(a) cultivating type 1 algae in an aqueous medium under conditions promoting photosynthetic growth by the type 1 algae,
  (i) harvesting the cultivated type 1 algae from the aqueous medium, and
  (ii) recovering carbohydrates from the harvested type 1 algae;

(b) cultivating type 2 algae in an aqueous medium in the presence of sufficient nutrients to promote heterotrophic growth, in the absence of light, wherein the provided nutrients optionally include nutrients, e.g., carbohydrates, extracted from the type 1 algae,
  (i) harvesting the cultivated type 2 algae from the aqueous medium, and
  (ii) recovering lipids, proteins, and/or carbohydrates from the harvested type 2 algae.

In a preferred embodiment, the type 1 algae is cultivated in an algae growth apparatus that includes a suitable reservoir or conduit that is exposed to sunlight, having at least one transparent wall to allow illumination of the type 1 algae by light, e.g., sunlight. Preferably, the algae growth apparatus also includes a reservoir or conduit that is buried in the ground for cultivating the type 2 algae. The type 1 algae aqueous medium is preferably circulated through a conduit by means of a suitable pump, wherein the conduit is in operative thermal contact with the aqueous medium of the type 2 algae. The operative thermal contact is optionally in the form of tubing immersed in the aqueous medium of the type 2 algae. Alternatively, an art standard heat exchanger, e.g., as commercially available from Alfa Laval, Slamex or Lackeb, may also be employed for this purpose. The circulation of the aqueous medium of the type 1 algae permits heat acquired during the illumination of the type 1 algae to be dissipated into the aqueous medium of the type 2 algae. This arrangement keeps both the type 1 and type 2 algae in a preferred temperature ranging from about 25° C. to about 35° C. Control of heat distribution is accomplished by controlling the speed of the circulating pump, and/or by supplemental cooling or heating as required.

Regulation of Temperature

Figure 1:
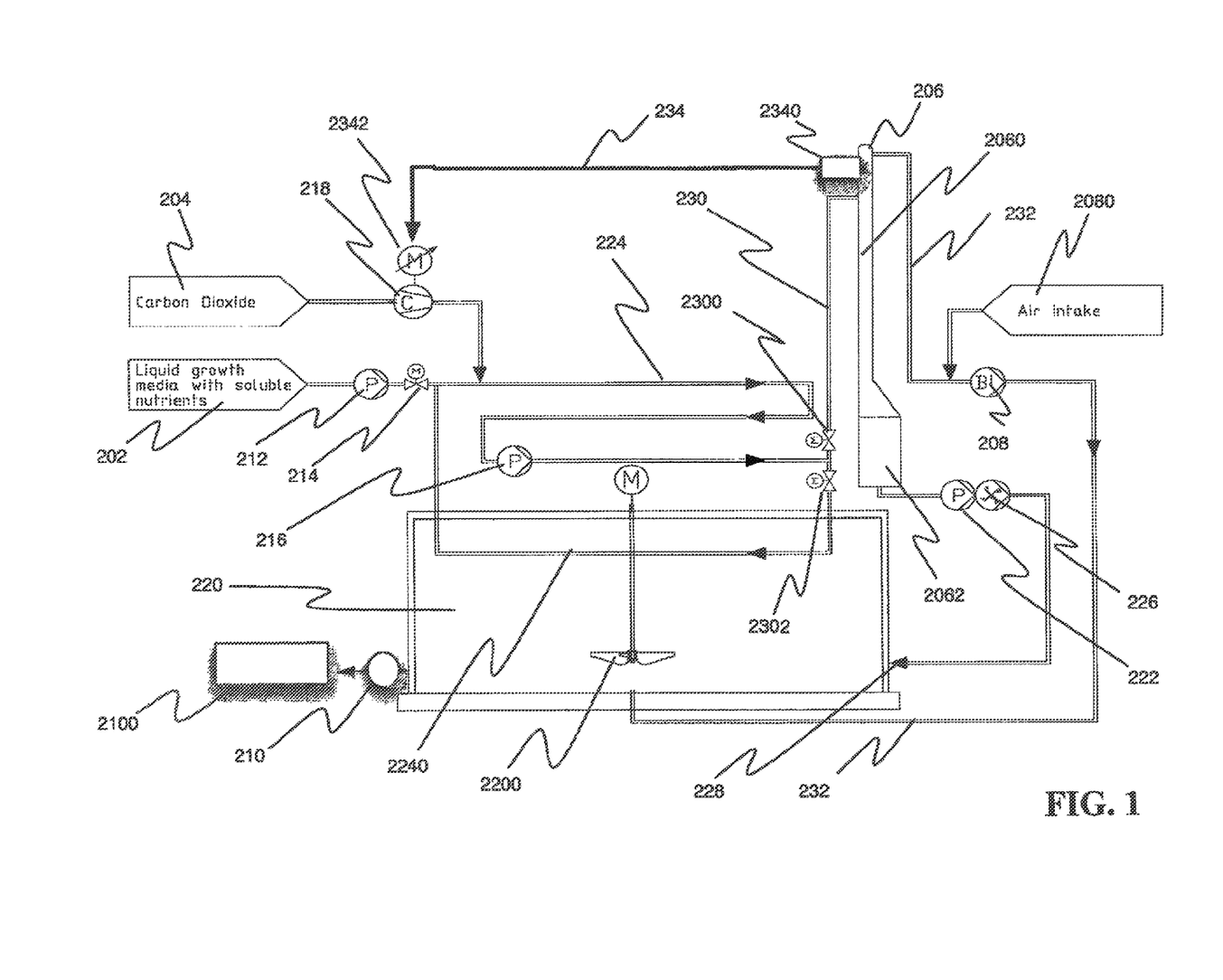
FIG. 1 illustrates an arrangement of conduits and reservoirs in one embodiment of thermal control in the algae growth system in accordance with the invention.

FIG. 1 illustrates one embodiment of a system capable of effecting thermal control in the algae growth system in accordance with the invention.

In FIG. 1, a conduit system 224 includes a first portion and a second portion subject to different thermal environments. For example, the first portion is often an above-ground portion exposed to sunlight and the resultant heating effect thereof while, the second portion is a below ground portion which is not exposed to sunlight.

Conduit system 224 comprises, for example, about 400 meters of pipe in the above ground aspect of the algae growth system. Circulation time of algae through the conduit system 224 is determined in one of various means involving flow equipment associated with the conduit system 224, including varying the speed of a pump 216 associated with the conduit system 224 and/or by altering the speed of inputting gaseous $CO_2$ to the conduit system 224 via a compressor or valve 218. Other regulating mechanism for regulating the circulating time may be provided.

Circulation time of the type 1 algae medium correlates with efficiency of heat exchange. Circulation direction of algae through the conduit system 224 is indicated with arrows in FIG. 1. Preferably, the circulation time is set so that the temperature of the algae during the time above the surface, i.e., in the above ground portion of conduit system 224, does not exceed about 35° C. Aspects of the underground portion 2240 of the conduit system 224, i.e., inside of a reservoir 220, are preferably constructed using steel for optimal heat transfer, relative to construction with plastics. For the heat exchanger, for example, flexible steel hose or pipe is employed in one embodiment, although other known flexible tubing or conduits are also envisioned to be within the scope and spirit of the invention. Flow to the underground part 2240 can be adjusted further with a valve 2302. The reservoir 220 is preferably constructed underground, although may be constructed in other locations to provide a lower temperature than the temperature to which the above ground portion of the conduit system 224 is exposed. The reservoir 220 optionally includes a means 2200 for stirring the content of the reservoir, e.g., a propellor or analogous stirring mechanism.

The temperature of the type 2 algae growth stage is preferably maintained at about 20° C. The system is dimensioned in a way that the type 1 algae pipe system warms the underground type 2 algae stage during the day, and then the type 2 algae stage keeps the type 1 algae warm during the night. The flow rate of the aqueous medium is controlled by a pump 216.

The flow rate correlates to the rate of heat transfer, and thus to the temperature of the respective type 1 and type 2 algae volumes.

Regulation of Gas Levels

In addition to thermal control, it is necessary to control the $CO_2$ levels, $O_2$ levels and nutrient flows among the two or more separately cultivated volumes of algae. One embodiment of the algae growth apparatus is illustrated by FIG. 1, as follows.

Nutrients, such as ammonia or ammonium and phosphorous compounds, which are dissolved in water, are stored in at least one reservoir 202. The water in reservoir 202 optionally includes dissolved $CO_2$. Pump 212 pumps nutrients and water from reservoir 202 to the algae growth apparatus via a valve 214. Pump 212 and valve 214 constitute a nutrient flow control mechanism or means. A carbon source, such as $CO_2$ gas or $CO_2$ in aqueous solution, is stored in at least one reservoir 204. $CO_2$ is fed from the reservoir 204 to the conduit system 224 of the algae growth apparatus via the compressor or valve 218. The compressor/valve 218 controls the $CO_2$ intake to the system, and thus constitutes a $CO_s$ intake control or regulating mechanism or means.

Compressor/valve 218 is controlled by a motor 2342 which receives control signals via a control/feedback line 234. The control line 234 receives control signal from a gas measurement sensor 2340. In a preferred embodiment, the compressor/valve 218 is a compressor that can feed gas to the conduit system 224 with pressure, and specifically, to the above-ground portion of the conduit system 224.

There is conduit 230 connected to conduit system 224 (and the underground portion 2240) directly or via a valve 2300. Conduit 230 has a substantially vertical portion, and may even be entirely vertical, and is referred to as a vertical conduit. The vertical conduit system 230 is used to enable higher than atmospheric pressure for the conduit system 224 (discussed below) and in addition, to work as a gas release system from the conduit system 224, as well as to work as conduit line to collect algae of type 1 from the conduit system 224. Vertical conduit 230 is connected to conduit system 224 in a way that enables gas to be collected (i.e., gas will go up in the vertical conduit 230 in view of the at least partly vertical orientation thereof).

Feedback line 234 provides a signal to the motor 2342 controlling the compressor/valve 218 to, for example, limit $CO_2$ flow if an excess amount of $CO_2$ gas is detected by the gas measurement sensor 2340 connected to a gas collection chamber 206. Collection chamber 206 is connected to the upper end of the vertical conduit 230. The gas measurement sensor 2340 is configured to analyze, the amount of $CO_2$ and/or oxygen ($O_2$) gas. Additionally, the feedback line 234 provides a signal to the motor 2342 controlling the compressor/valve 218 to, for example, increase $CO_2$ flow if amount of $O_2$ gas is detected by the gas measurement sensor 2340 to be lower than expected by rate of photosynthesis. In normal operation, the top part 2060 of the collection chamber 206 fills up with the gas containing mainly $O_2$ but also typically some $CO_2$. Gas collection chamber 206 can have valve or means to release excess amount of gas. The gas collection chamber might have open top or substantially open top.

Alternatively, the feedback line 234 will adjust the compressor/valve 218 to enhance $CO_2$ flow if insufficient $CO_2$ is detected by sending an appropriate control signal to the motor 2342. In this manner, the $CO_2$ content of the growth medium is maintained at optimal levels depending on or as a function of the algae type and concentration.

In order to appreciate the parameters related to control of $CO_2$ and $O_2$ content of the growth system, the following information is provided.

An overall equation describing photosynthesis is: $6CO_2 + 6H_2O + light \rightarrow C_6H_{12}O_6 + 6O_2$, i.e., $CO_2$ and water (+light) form sugars and oxygen. In steady state situation amount of $CO_2$ fed in the system should be substantially same as amount of $O_2$ released (and collected by gas collection chamber 206). Sugars are used by algae to grow and multiply. The growth rate of algae is proportional to the amount of $CO_2$ in the liquid (Kezhen Ying (Department of Chemical and Biological Engineering, University of Sheffield, UK), et al., "Microalgal growth enhancement by microbubble induced airlift loop bioreactor—the effect of dosing flow rate," available as a PDF download on the internet at eyrie.shef.ac.uk/steelCO2/open/algaescreen.pdf; see also, Zimmerman et al., 2011 *Applied Energy* 88(10): 3357-3369—Special Issue of Energy from algae: Current status and future trends).

In an open pond algae growth system, the pond is under normal atmospheric pressure conditions. Since the amount of $CO_2$ which can be dissolved in water under normal atmospheric pressure is limited, the algal growth rate is also limited.

Table 2 below shows some solubility values at a temperature of 15° C. The values are extracted from IUPAC-NIST Solubility Database NIST Standard Reference Database 106/National Institute of Standards and Technology/US department of Commerce as found on the NIST website.

TABLE 2

| Pressure [bar] | Solubility |
| --- | --- |
| 0.947 | 0.9441 |
| 1.096 | 1.1619 |
| 11.736 | 1.8647 |
| 1.977 | 2.1623 |
| 2.686 | 2.9076 |
| 2.935 | 3.1764 |
| 3.175 | 3.4857 |
| 3.422 | 3.7152 |
| 3.668 | 4.0031 |
| 4.163 | 4.5006 |

For Table 2, solubility is reported in units of one unit volume of gaseous $CO_2$ per one unit of water. As it can be seen from the table, solubility of $CO_2$ in water increases with pressure. In an embodiment where the height of the vertical conduit 230 is 10 meters, this height of aqueous medium introduces an additional pressure of 1 bar, relative to horizontal conduit 224, thus doubling the $CO_2$ concentration available in the aqueous medium.

Example Amounts of $CO_2$ Solubility in Water (Aqueous Medium).

Amount of $CO_2$ which can be dissolved in water at a particular temperature (e,g.,15° C.) temperature in 1 bar is 2.27 g/liter. (Calculated as 1.16 liter/(22.4 liter/mole)–0.0518 moles. 0.0518 molex(12 g/mole+32 g/mole)=2.27 g)

Amount of $CO_2$ which can be dissolved to water at said (15° C.) temperature in 2 bars is 4.24 g/liter. (Calculated as 2.16 liter/(22.4 liter/mole)=0.0964 moles. 0.0964 molex(12 g/mole+32 g/mole)=4.24 g).

Referring back to FIG. 1, in this embodiment of the algae growth system, the presence of the vertical conduit 230 enables higher than about 2.27 g/liter $CO_2$ solubility in the system. The vertical conduit 230 can be, for example, from about 10 to about 30 meters or greater in height, e.g., 10 meters (for up to about 4.2 g/liter) or 20 meters or 30 meters or more if greater amounts of $CO_2$ are needed in the system.

The cross sectional area of the vertical conduit 230 can range from about 10 cm² to about 30 cm² or greater, depending on the capacity of the algae growth system.

Referring again back to FIG. 1, the vertical conduit 230 introduces hydrostatic pressure to the algae type 1 conduit system since the pressure of a liquid is proportional to the depth (i.e., the height of the vertical conduit 230). Vertical conduit 230 is connected from the top to the gas collection chamber 206. The algae type 1 growth process produces $O_2$ that is optionally used to support or enhance algae type 2 growth. The $O_2$ gas is optionally delivered to the reservoir 220 via a conduit 232 using a pump 208. Additional air can be injected to the system via an air intake device 2080, e.g., via a compressor.

Alternatively, the gas collection chamber 206 optionally collects any $CO_2$ which has not been dissolved into the water, or has not been used by algae type 1. The excess $CO_2$ can be recirculated, e.g., via reservoir 204 and/or it can be delivered using pump 208 to support the algae type 2 growth cycle.

Alternatively, the gas collection chamber 206 does not collect gas but releases it to back to atmosphere i.e. gas collection chamber can have substantially open top setting the pressure level of the top of the vertical conduit 230 to atmospheric pressure. If the chamber is closed the pressure in the chamber can be used further to increase hydrostatic pressure introduced by conduit 230.

The algae type 1 is harvested from the algae growth apparatus from time to time or continuously. The harvested algae type 1 includes sugars which can be used to feed the algae type 2. Referring again back to FIG. 1, algae type 1 is collected/harvested from the conduit system 224 by adding an amount of liquid in the system from nutrient reservoir 202. When the amount of liquid is higher than total volume of conduit system 224 (and belowground portion thereof 2240) and vertical conduit 230, the algae and liquid will "spill over" and drop to a bottom part 2062 of the collection chamber 206.

Referring again back to FIG. 1, the algae type 1 biomass is processed at a processing unit 226 to release cellular contents, and the extracted sugars and other nutrients are pumped to the reservoir 220 via a pump 222. Sugars, water and other nutrients are fed to the algae type 2 growth stage via an inlet 228 to the reservoir 220. There is a mechanism 2200 to stir the algae type 2 in the reservoir 220. Stirring is desired in order to ensure movement of the liquid in the reservoir 220 for heat transfer purposes as well as ensure that the algae does not stick to the bottom of the reservoir 220.

Harvesting Algae Type 1 and 2.

Figure 2:
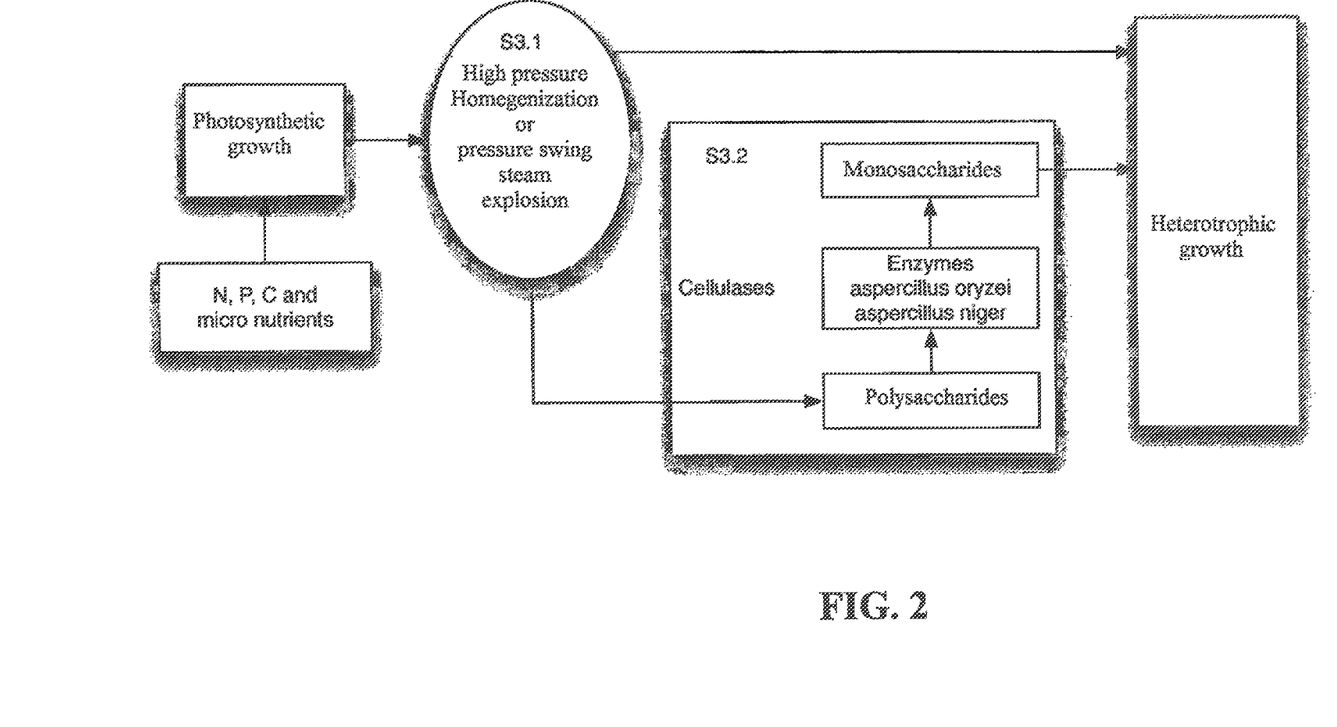
FIG. 2 illustrates an exemplifying embodiment of processing steps within 226 of FIG. 1.

FIG. 2 illustrates an exemplary embodiment of processing steps within the processing unit 226 of FIG. 1.

In FIG. 2, step S3.1 the harvested algae type 1 is subjected to high pressure homogenization or pressure swing steam explosion to rupture the algae cellular structure. In addition to mechanical disruption of cellular structures, cellulase enzyme, e.g., derived from *aspercillus oryzei* or *aspercillus niger*, are optionally introduced at step S3.2 in order to hydrolyze algal polysacharides to monosacharides.

Figure 3:
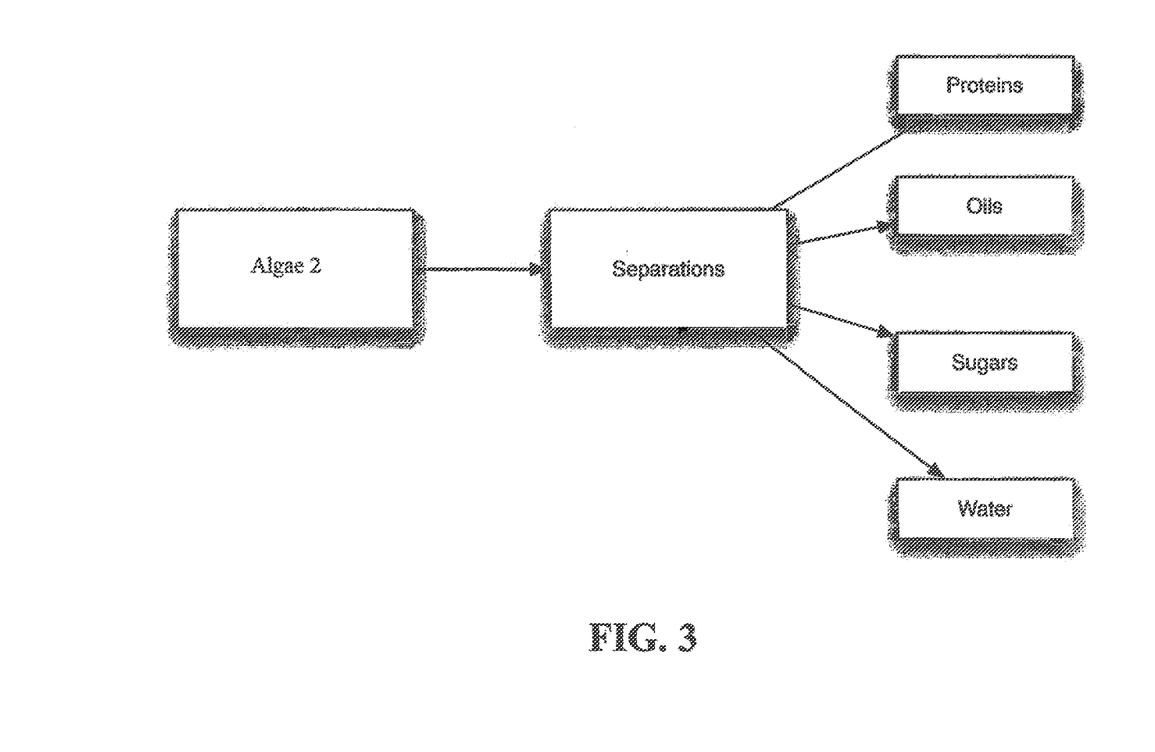
FIG. 3 illustrates that the harvested algae type 2, is extracted to obtain, e.g., proteins, oils, sugars and water.

Algae type 2 is harvested from the reservoir 220 of FIG. 1 continuously or from time to time via a pump 210 of FIG. 1 leading to an outtake container 2100. As illustrated by FIG. 3, algal oil and other substances are then extracted from the harvested algae type 2, e.g., proteins, oils, sugars and water.

The extracted materials are either marketed or recycled into the algae cultivation process. For example proteins are optionally processed to release ammonia to feed the algae, and sugars are optionally fed back to the algae type 2 growth reservoir. Water from the process is sterilized and purified before it is reintroduced to the back to the algae growth apparatus.

Regulation of Temperature and Gas Pressure

Figure 5:
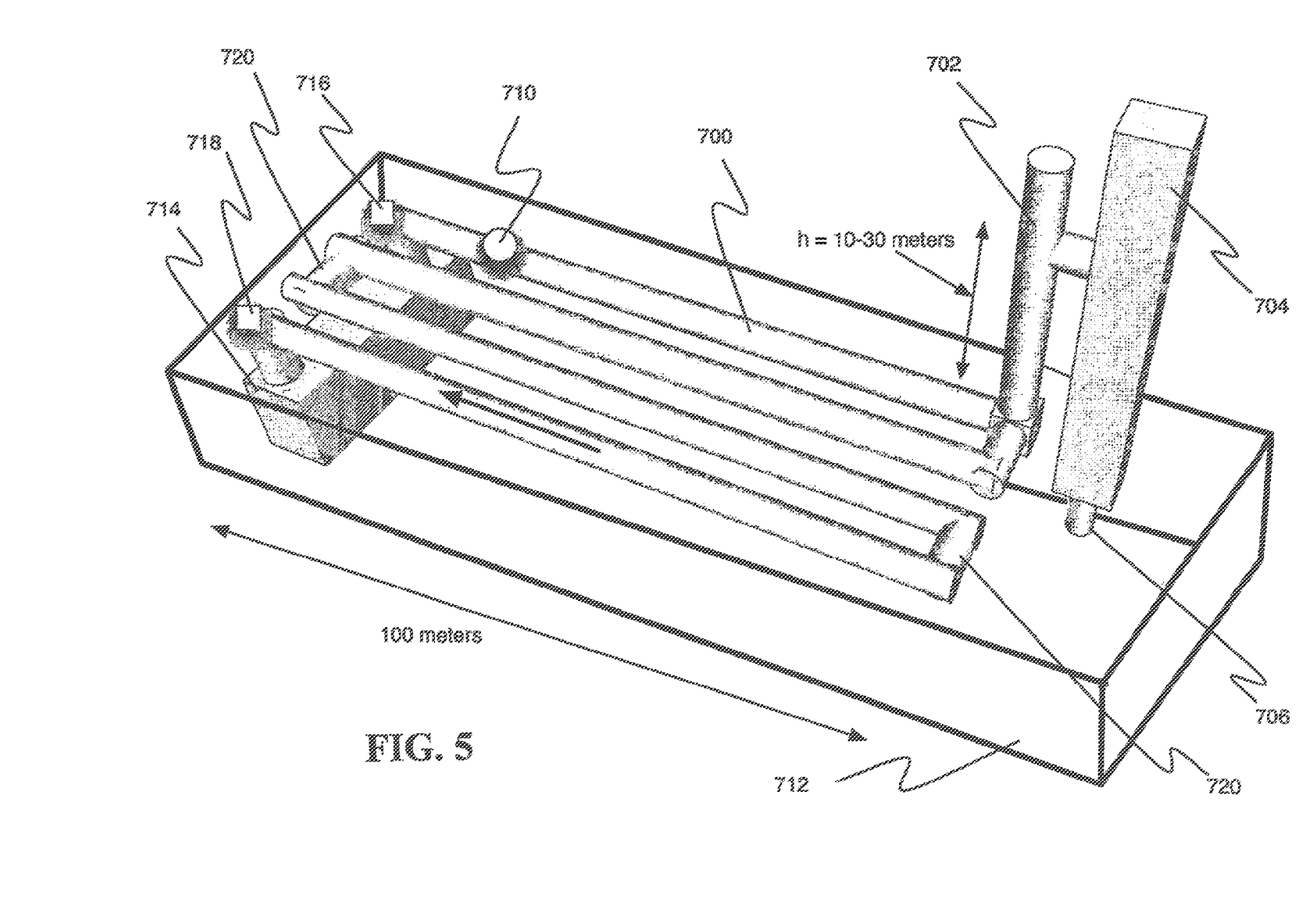
FIG. 5 illustrates an exemplifying embodiment of the inventive apparatus in three dimensions.

FIG. 5 shows a three-dimensional (3D) illustration of an embodiment of the conduit system illustrated by the schematic of FIG. 1. The algae type 1 (photosynthesis based algae) flows in a series of elongate conduits 700 substantially parallel to one another and arranged alongside one another, and that are fluidly interconnected to each other via connections 720 at their ends to form a serpentine path. In one embodiment, and simply by way of example, the dimensions of the system are as follows: each conduit 700 is about 100 meters and has a diameter of about 100 mm, i.e., a total length is about 400 meters (four conduits) with total volume of 3.14 cubic meters. The conduit system includes a pressure maintaining column/conduit 702 (a vertical conduit). Vertical conduit 702 can be connected to collection chamber 704 (representing a particular embodiment of the gas collection chamber 206 of FIG. 1). As discussed earlier algae from the first growth phase in conduit 700 is harvested via the chamber 704. The algae type 1 biomass is processed at a processing unit 706 (refer to 226 in FIG. 1) to release cellular contents, and the extracted sugars and other nutrients are pumped to the reservoir 712. Algae in conduit system 700 is circulated with pump 710.

The algae type 1 aqueous medium is circulated via a conduit 714 which is in the reservoir 712 below the ground, and acts as a heat exchanger. Algae type 2 grows in the reservoir 712. The above ground conduit system is connected to the underground conduit system at points 716 and 718. Heat is exchanged via the conduit 714, which is preferably made of steel. Cooled (or during the night warmed) type 1 algae aqueous media flows back above the ground at point 716 from the reservoir 712. The arrow in FIG. 5 illustrates the direction of circulation.

Figure 4:
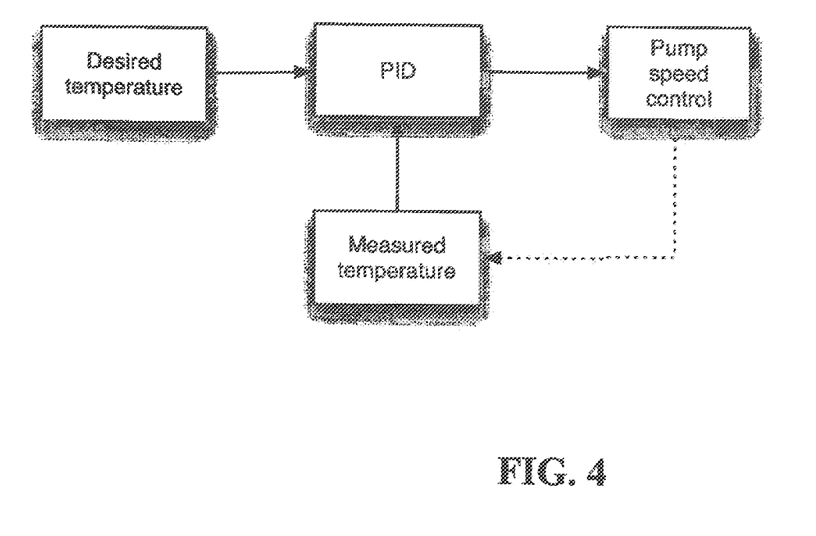
FIG. 4 illustrates control parameters for a PID controller (Proportional, Integral, Derivative) to regulate the operation of the circulating pump and thereby the heat transfer rate between the light and dark aspects of algae growth apparatus.

Referring again to FIG. 5, the temperature of the algae type 1 aqueous medium is measured from at least in conduit 718 and from point 716 to determine the effect of cooling/heating introduced to the algae aqueous medium circulated in contact with the reservoir 712. The temperatures are used as control parameters for a PID controller (Proportional, Integral, Derivative) which controls the speed of a circulation pump 710 arranged in connection with one of the conduits 700 as illustrated by FIG. 4. If the circulation rate is decreased, the algae has more time to heat up in direct sun light than in the presence of more rapid circulation. As an example, direct sunlight has energy output of about 1 kWatt/m$^2$. Assuming 50% heat absorption the 400 m×0.1 m=40 m$^2$ area of algae containing conduits 700 will receive a total of 0.5×40×1 kWatt=20 kWatt of energy.

Using initial temperature of 20° C. (i.e., temperature of algae type 2 medium in the reservoir 712) at point 716 and allowing a temperature increase of 10° C. to 30° C. at point 718, the total amount of energy which can be absorbed without going below the maximum temperature is E=4.18 kJ/kg/° C. ×10° C.×3140 kg=131252 kJ.

With 20 kWatt of energy input from sun it will take 131252 kJ/20kWatt/s=3200 seconds, i.e., in this scenario, the algae 1 type 1 aqueous medium has to be moved at least once per 3200 second from point 716 to point 718 for cooling. In the case of having higher heat absorption by the algae type 1 aqueous medium, for example, in an embodiment where the density of the algae type 1 is high, the absorption % could be close to 100%. In order to keep temperature within the range of about 20° C. to about 45° C., a speed of twice per 3200 sec, i.e., once per 1600 sec is required. Thus, the apparatus and methods permits adaptation to variable heat absorption by the algae type 1 aqueous medium during illumination periods. The heat absorption is function of algae density. In the start of the growth phase density is low and as the algae population grows the density is higher.

Simplified View

Figure 6:
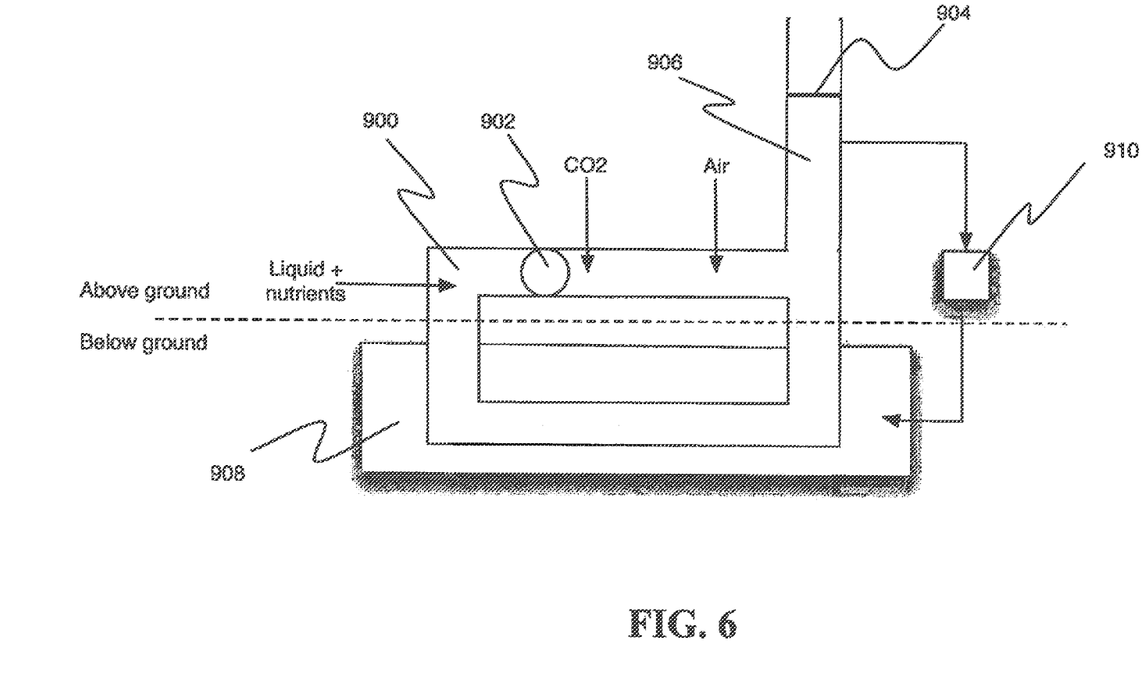
FIG. 6 illustrates a simplified overview of the inventive apparatus.

FIG. 6 shows a simplified view of a particular embodiment of the inventive apparatus. Liquids and nutrients are fed in a substantially horizontal conduit 900 where algae type 1 grows. Pump 902 is used to circulate the algae to enable heat transfer to one or more underground reservoir 908. Vertical conduit 906 is connected to the conduit 900. The liquid level 904 in vertical conduit 906 is substantially higher than the level of the conduit 900. Vertical conduit 906 might be, in some embodiments, open at the top to allow gas to exit to the atmosphere. According to some embodiments, $CO_2$ is fed to conduit 902 (see liquid and nutrients with the directional arrow in FIG. 6). During the photosynthesis, oxygen is produced by algae. Air is fed to conduit 900 to enable "washup" of excess dissolved oxygen from the liquid. Algae of type 1 is harvested via means of an algae withdrawal system 910 (such as discussed earlier, see the description of FIG. 2) connected to the vertical conduit 906 and if desired, fed to reservoir 908 with algae type 2. According to another embodiment, a possible change in pH level due to solvent CO2 can be compensated by adding neutralizing chemicals.

Example Plant

Figure 7:
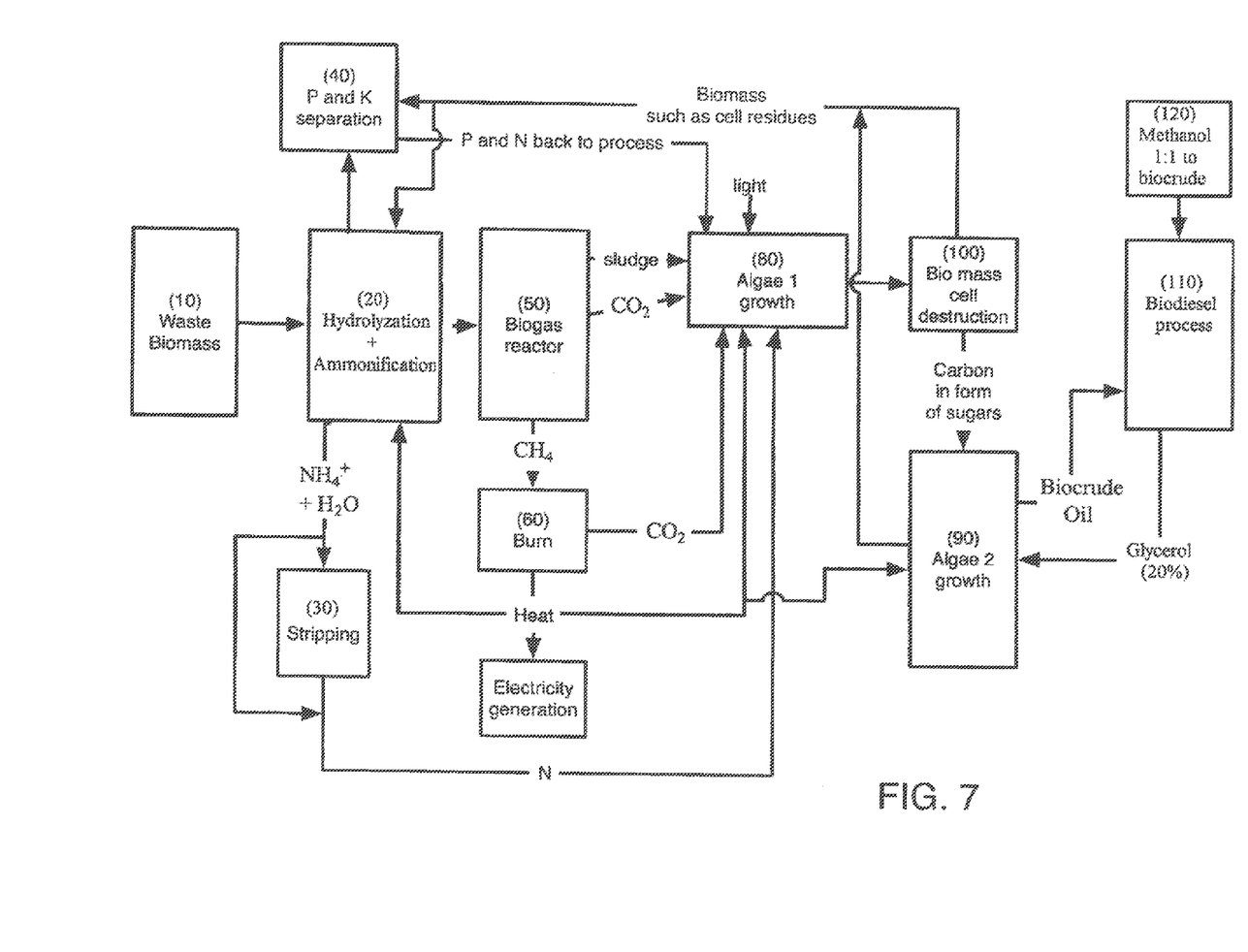
FIG. 7 illustrates an example environment for the inventive apparatus and process steps.

FIG. 7 shows an overview of some of the steps and embodiments of the process. Waste biomass 10 such as slaughter waste and meat bone meal (MBM), fish bones etc. other organic matter is processed using method of hyrdolization and ammonification 20 to extract nitrogen in form of ammonia/ammonium from the waste for example using microorganisms as described in co-owned U.S. patent application Ser. No. 13/722,228, incorporated by reference herein in its entirety. Nitrogen/ammonia is extracted from the water with conventional methods of stripping 30. Ammonia or nitrogen of the ammonia is used by algae growth process. Alternatively ammonium+water can be used directly or as concentrate as nutrient source for the algae growth 1 phase 80.

Phosphorous (P) and potassium (K) are separated using bio or other process 40 from the residuals of hydrolysis and ammonification process 20. P and K are provided to algae 1 growth process 80.

In addition, micro nutrients such as Ni, Mg, Mn, Fe, Zn are provided to the growth process 80. Based on embodiments micro nutrients such as Ni, Mg, Mn, Fe, Zn etc. are added to algae stage 1 80 or/and algae stage 2 90. Source materials used for ammonization process can provide some or all of the micro nutrients for the process.

Biogas reactor 50 produces as side product $CO_2$ and as main product $CH_4$. $CH_4$ can be burned 60 to form $CO_2$ for algae growth stage 80 (and for algae growth phase 90). In addition to CO2 from internal process 60, external $CO_2$ sources can be used from other industries or from power plants or from any machine using fossil fuels. Algae type 1 is preferably a photosynthesis type of algae which uses sun light or other illumination as main energy source as discussed earlier. Heat produced by methane burn can be used as heat source or it can be used to generate electricity.

Algae from algae growth phase 80 is harvested and carbons as form of sugars are extracted in biomass cell destruction phase 100. The sugars are used as feedstock for algae 2 in algae 2 growth phase 90. Residuals from biomass cell destruction phase 100 and algae 2 growth stage 90 can be send back to hydrolyis and ammonification process 20 and to P and K separation phase 40 to recover and circulate nutrients in the system.

Harvested biocrude from algae type 2 from algae 2 growth stage 90 is used in transesterification process 110 to form biofuel such as biodiesel. Typically methanol 120 is added to biocrude in the process. Further to ensure efficient usage of materials reciduals (such as glycerol) from transesterification process are used as feedstock for algae.

INCORPORATION BY REFERENCE

Numerous references are cited throughout this application, each of which is incorporated by reference herein in its entirety.

What is claimed is:

1. An algae cultivation system, comprising:
    a conduit system for cultivating a first type of algae, having a portion exposed to illumination and a second portion occluded from illumination;
    a flow mechanism for causing movement of a first type of algae, in an aqueous medium through said conduit system;
    a heat exchanger for cultivating a second type of algae, in thermal contact with said second portion of said conduit system, said second portion passing the first type of algae, in the aqueous medium;
    a source of algae nutrients;
    a first flow regulating system that regulates flow of algae nutrients from said source of algae nutrients into said first portion of said conduit system;
    a source of carbon dioxide;
    a second flow regulating system that regulates carbon dioxide flow from said source of carbon dioxide into said first portion of said conduit system;
    a vertical conduit connected to said first portion of said conduit system and extending vertically upward from said first portion of said conduit system to introduce hydrostatic pressure to said first portion of said conduit system;
    a collection chamber communicating with an upper end region a said vertical conduit, said second flow regulating system being controlled based on characteristics of gas in said collection chamber; and
    an algae processing unit which processes algae from said first portion of said conduit system, wherein the algae is collected via the vertical conduit and the collection chamber, to extract sugar, water and algae nutrients and directing the extracted sugar, water and algae nutrients into said heat exchanger to interact with the second type of algae therein;
    wherein the first portion of said conduit system is partially or entirely transparent to the illumination.

2. The algae cultivation system of claim 1, wherein said second portion of said conduit system is situated underground.

3. The algae cultivation system of claim 1, wherein said first portion of said conduit system includes a plurality of elongate conduits substantially parallel to one another and connected at adjacent ends to form a serpentine travel path for the first type of algae.

4. The algae cultivation system of claim 1, wherein said flow mechanism comprises a pump associated with said first portion of said conduit system.

5. The algae cultivation system of claim 1, wherein said second flow regulating system comprises a motor and a compressor/valve controlled by said motor, said motor being controlled by command signals generated based on the characteristics of the gas in said collection chamber.

6. The algae cultivation system of claim 5, further comprising a measurement sensor associated with said collection chamber for measuring carbon dioxide in said collection chamber and generating command signals for said motor based thereon.

7. The algae cultivation system of claim 1, wherein said vertical conduit is from about 10 meters to about 30 meters in height extending upward from said conduit system.

8. The algae cultivation system of claim 1, further comprising a third flow regulating system that regulates a flow of oxygen from said collection chamber into the interior of said heat exchanger to interact with the second type of algae therein.

9. The algae cultivation system of claim 8 wherein the third flow regulating system comprises a conduit that regulates oxygen gas flow to the aqueous medium of said heat exchanger, and a pump.

10. The algae cultivation system of claim 1 wherein the algae processing unit is a high pressure homogenizer or a pressure swing steam explosion unit.

11. The algae cultivation system of claim 1 wherein the flow mechanism comprises a pump and a Proportional, Integral, Derivative (PID) controller.

12. The algae cultivation system of claim 1, wherein said heat exchanger comprises the second portion of said conduit that is immersed in a reservoir for cultivating the second type of algae.

13. The algae cultivation system of claim 1, wherein said second portion of said conduit system comprises hose or pipe.

14. The algae cultivation system of claim 13, wherein the hose or pipe is comprised of steel.

15. The algae cultivation system of claim 14, wherein the hose or pipe is flexible.

16. The algae cultivation system of claim 1, wherein the collection chamber is fluidly connected to the algae processing unit, and the algae processing unit is fluidly connected to the heat exchanger by an inlet for directing the extracted sugar, water and algae nutrients into said heat exchanger.

17. A process for the cultivation of algae with the algae cultivation system of claim 1, comprising the steps of:
    (a) growing the first type of algae in an aqueous medium in the conduit system,
        (i) harvesting the first type of algae from the aqueous medium via the vertical conduit and the collection chamber, and
        (ii) recovering carbohydrates from the harvested first type of algae using the algae processing unit;
    (b) growing the second type of algae in an aqueous medium in the presence of sufficient nutrients to promote heterotrophic growth, in the heat exchanger, wherein the nutrients comprise carbohydrates extracted from the first type of algae,
        (i) harvesting the second type of algae from the aqueous medium of said heat exchanger and
        (ii) recovering lipids, proteins, and/or carbohydrates from cells of the harvested second type of algae.

18. The process of claim 17 wherein the illumination of the first portion of said conduit system is from sunlight.

19. The process of claim 18 wherein the sunlight imparts thermal energy to the first portion and said thermal energy is distributed to the second portion to maintain temperatures in a range of from about 20° C. to about 45° C.

20. The process of claim 17 wherein the algae nutrients further comprise oxygen collected from said collection chamber.

\* \* \* \* \*